(12) United States Patent
Luo et al.

(10) Patent No.: US 11,299,527 B2
(45) Date of Patent: Apr. 12, 2022

(54) LONG-ACTING RECOMBINANT PORCINE FSH FUSION PROTEIN AND PREPARATION METHOD AND APPLICATION THEREOF

(71) Applicant: BEIJING VJT BIO CO., LTD., Beijing (CN)

(72) Inventors: Haoshu Luo, Beijing (CN); Lei Shi, Beijing (CN); Guo Han, Beijing (CN)

(73) Assignee: BEIJING VJT BIO CO., LTD.

( * ) Notice: Subject to any disclaimer, the term of this patent is extended or adjusted under 35 U.S.C. 154(b) by 0 days.

(21) Appl. No.: 16/609,543

(22) PCT Filed: Nov. 1, 2017

(86) PCT No.: PCT/CN2017/108854
§ 371 (c)(1),
(2) Date: Oct. 30, 2019

(87) PCT Pub. No.: WO2019/051954
PCT Pub. Date: Mar. 21, 2019

(65) Prior Publication Data
US 2020/0223896 A1    Jul. 16, 2020

(30) Foreign Application Priority Data
Sep. 15, 2017 (CN) .......................... 201710833452.1

(51) Int. Cl.
| C07K 14/59 | (2006.01) |
| A61K 47/68 | (2017.01) |
| C12N 15/62 | (2006.01) |
| C12N 15/85 | (2006.01) |
| A61K 38/00 | (2006.01) |

(52) U.S. Cl.
CPC .............. *C07K 14/59* (2013.01); *A61K 47/68* (2017.08); *C12N 15/62* (2013.01); *C12N 15/85* (2013.01); *A61K 38/00* (2013.01); *C07K 2319/30* (2013.01)

(58) Field of Classification Search
None
See application file for complete search history.

(56) References Cited

U.S. PATENT DOCUMENTS

| 9,969,786 B2 | 5/2018 | Xu et al. |
| 10,023,624 B2 | 7/2018 | Hou et al. |
| 2005/0186662 A1 | 8/2005 | Low |
| 2014/0308706 A1* | 10/2014 | Kuo ........................ A61P 31/12 435/69.51 |
| 2016/0060321 A1* | 3/2016 | Xu ........................ C07K 14/59 424/134.1 |
| 2017/0174736 A1* | 6/2017 | Hou ........................ A61P 15/08 |
| 2018/0362610 A1 | 12/2018 | Hou et al. |

FOREIGN PATENT DOCUMENTS

| CN | 103509121 A | 1/2014 |
| CN | 103539860 A | 1/2014 |
| CN | 103539862 A | 1/2014 |
| CN | 103554268 A | 2/2014 |
| CN | 2924049 * | 9/2015 ............. C07K 14/59 |
| CN | 106496331 A | 3/2017 |

OTHER PUBLICATIONS

Siegel et al., Reproductive Sciences 20(3) 211-233 (Year: 2013).*
Piche-Nicholas et al., MAbs. 2018; 10: 81-94. doi: 10.1080/19420862.2017.1389355 (Year: 2018).*
International Search Report for International Application No. PCT/CN2017/108854; dated May 14, 2018 (4 pages).

\* cited by examiner

*Primary Examiner* — Christina M Borgeest
(74) *Attorney, Agent, or Firm* — Mendelsohn Dunleavy, P.C.

(57) ABSTRACT

Two long-acting recombinant porcine FSH (follicle-stimulating hormone) fusion proteins, comprising pFSH-Fc-1 and pFSH-Fc-2. α subunit/β subunit is directly or indirectly fused on a Fc fragment by means of a linking component; the β subunit/α subunit is combined with the α subunit/β subunit by means of a Van der Waals force or the linking component. The porcine FSH fusion proteins can be prepared by an eukaryotic expression system based on a gene engineering technology. The two porcine FSH fusion proteins have a good medicinal effect and have a longer half-life period as compared with that of a natural porcine FSH; the two porcine FSH fusion proteins do not generate an undesirable effect on animals and can replace pregnant mare serum gonadotropin (PMSG) to be used in animal breeding production. The two porcine FSH fusion proteins can be used for preparation of medicines in the field of animal breeding.

17 Claims, 3 Drawing Sheets
Specification includes a Sequence Listing.

SEQUENCE LISTING

```
<160> NUMBER OF SEQ ID NOS: 10

<210> SEQ ID NO 1
<211> LENGTH: 96
<212> TYPE: PRT
<213> ORGANISM: Sus scrofa

<400> SEQUENCE: 1

Phe Pro Asp Gly Glu Phe Thr Met Gln Gly Cys Pro Glu Cys Lys Leu
1               5                   10                  15

Lys Glu Asn Lys Tyr Phe Ser Lys Leu Gly Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Ala Arg Val
65                  70                  75                  80
```

Glu Asn His Thr Glu Cys His Cys Ser Thr Cys Tyr Tyr His Lys Ser
                85                  90                  95

<210> SEQ ID NO 2
<211> LENGTH: 288
<212> TYPE: DNA
<213> ORGANISM: Artificial Sequence
<220> FEATURE:
<223> OTHER INFORMATION: Sus scrofa

<400> SEQUENCE: 2
ttccctgacg gcgagttcac catgcagggc tgccccgagt gcaagctgaa ggagaacaag      60
tacttctcca agctgggcgc ccccatctac cagtgcatgg gctgctgctt ctcccgggct     120
taccctaccc ctgcccggtc caagaagacc atgctggtgc caagaacat cacctccgag     180 gccacctgtt gcgtggccaa ggccttcacc aaggccaccg tgatgggcaa cgccagggtg     240
gagaaccaca ccgagtgcca ctgcagcacc tgctactacc acaagtcc                 288

<210> SEQ ID NO 3
<211> LENGTH: 109
<212> TYPE: PRT
<213> ORGANISM: Sus scrofa

<400> SEQUENCE: 3

Cys Glu Leu Thr Asn Ile Thr Ile Thr Val Glu Lys Glu Glu Cys Asn
1               5                   10                  15

Phe Cys Ile Ser Ile Asn Thr Thr Trp Cys Ala Gly Tyr Cys Tyr Thr
            20                  25                  30

Arg Asp Leu Val Tyr Lys Asp Pro Ala Arg Pro Asn Ile Gln Lys Thr
        35                  40                  45

Cys Thr Phe Lys Glu Leu Val Tyr Glu Thr Val Lys Val Pro Gly Cys
    50                  55                  60

Ala His His Ala Asp Ser Leu Tyr Thr Tyr Pro Val Ala Thr Glu Cys
65                  70                  75                  80

His Cys Gly Lys Cys Asp Ser Asp Ser Thr Asp Cys Thr Val Arg Gly
                85                  90                  95

Leu Gly Pro Ser Tyr Cys Ser Phe Ser Glu Met Lys Glu
            100                 105

<210> SEQ ID NO 4
<211> LENGTH: 327
<212> TYPE: DNA
<213> ORGANISM: Artificial Sequence
<220> FEATURE:
<223> OTHER INFORMATION: Sus scrofa

<400> SEQUENCE: 4
tgcgaactca caaacatcac catcaccgtg gaaaaggagg agtgcaactt ctgcatcagc      60
atcaacacca cctggtgcgc cggctattgc tatacaaggg atctggtcta caaggacccc     120
gccaggccca acatccagaa gacatgcacc ttcaaggagc tggtgtatga aaccgtgaag     180
gtccccggat gcgcccatca cgccgattcc ctgtacacct accccgtggc taccgagtgc     240
cattgcggca gtgcgactc cgactccacc gattgtacag tgaggggcct cggaccctcc     300
tactgctcct ttagcgagat gaaggag                                         327

<210> SEQ ID NO 5
<211> LENGTH: 221
<212> TYPE: PRT

<213> ORGANISM: Sus scrofa

<400> SEQUENCE: 5

Ile Cys Pro Ala Cys Glu Ser Pro Gly Pro Ser Val Phe Ile Phe Pro
1               5                   10                  15

Pro Lys Pro Lys Asp Thr Leu Met Ile Ser Arg Thr Pro Gln Val Thr
            20                  25                  30

Cys Val Val Val Asp Val Ser Gln Glu Asn Pro Glu Val Gln Phe Ser
        35                  40                  45

Trp Tyr Val Asp Gly Val Glu Val His Thr Ala Gln Thr Arg Pro Lys
    50                  55                  60

Glu Glu Gln Phe Asn Ser Thr Tyr Arg Val Val Ser Val Leu Pro Ile
65                  70                  75                  80

Gln His Gln Asp Trp Leu Asn Gly Lys Glu Phe Lys Cys Lys Val Asn
                85                  90                  95

Asn Lys Asp Leu Pro Ala Pro Ile Thr Arg Ile Ile Ser Lys Ala Lys
            100                 105                 110

Gly Gln Thr Arg Glu Pro Gln Val Tyr Thr Leu Pro Pro His Ala Glu
        115                 120                 125

Glu Leu Ser Arg Ser Lys Val Ser Ile Thr Cys Leu Val Ile Gly Phe
    130                 135                 140

Tyr Pro Pro Asp Ile Asp Val Glu Trp Gln Arg Asn Gly Gln Pro Glu
145                 150                 155                 160

Pro Glu Gly Asn Tyr Arg Thr Thr Pro Pro Gln Gln Asp Val Asp Gly
                165                 170                 175

Thr Tyr Phe Leu Tyr Ser Lys Phe Ser Val Asp Lys Ala Ser Trp Gln
            180                 185                 190

Gly Gly Gly Ile Phe Gln Cys Ala Val Met His Glu Ala Leu His Asn
        195                 200                 205

His Tyr Thr Gln Lys Ser Ile Ser Lys Thr Pro Gly Lys
    210                 215                 220

<210> SEQ ID NO 6
<211> LENGTH: 332
<212> TYPE: PRT
<213> ORGANISM: Artificial Sequence
<220> FEATURE:
<223> OTHER INFORMATION: Laboratory synthesis

<400> SEQUENCE: 6

Phe Pro Asp Gly Glu Phe Thr Met Gln Gly Cys Pro Glu Cys Lys Leu
1               5                   10                  15

Lys Glu Asn Lys Tyr Phe Ser Lys Leu Gly Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Ala Arg Val
65                  70                  75                  80

Glu Asn His Thr Glu Cys His Cys Ser Thr Cys Tyr Tyr His Lys Ser
                85                  90                  95

Gly Gly Gly Gly Ser Gly Gly Gly Ser Gly Gly Gly Ser Ile
            100                 105                 110

Cys Pro Ala Cys Glu Ser Pro Gly Pro Ser Val Phe Ile Phe Pro Pro
        115                 120                 125

-continued

```
Lys Pro Lys Asp Thr Leu Met Ile Ser Arg Thr Pro Gln Val Thr Cys
        130                 135                 140
Val Val Val Asp Val Ser Gln Glu Asn Pro Glu Val Gln Phe Ser Trp
145                 150                 155                 160
Tyr Val Asp Gly Val Glu Val His Thr Ala Gln Thr Arg Pro Lys Glu
                165                 170                 175
Glu Gln Phe Asn Ser Thr Tyr Arg Val Val Ser Val Leu Pro Ile Gln
            180                 185                 190
His Gln Asp Trp Leu Asn Gly Lys Glu Phe Lys Cys Lys Val Asn Asn
        195                 200                 205
Lys Asp Leu Pro Ala Pro Ile Thr Arg Ile Ile Ser Lys Ala Lys Gly
210                 215                 220
Gln Thr Arg Glu Pro Gln Val Tyr Thr Leu Pro Pro His Ala Glu Glu
225                 230                 235                 240
Leu Ser Arg Ser Lys Val Ser Ile Thr Cys Leu Val Ile Gly Phe Tyr
                245                 250                 255
Pro Pro Asp Ile Asp Val Glu Trp Gln Arg Asn Gly Gln Pro Glu Pro
            260                 265                 270
Glu Gly Asn Tyr Arg Thr Thr Pro Pro Gln Gln Asp Val Asp Gly Thr
        275                 280                 285
Tyr Phe Leu Tyr Ser Lys Phe Ser Val Asp Lys Ala Ser Trp Gln Gly
290                 295                 300
Gly Gly Ile Phe Gln Cys Ala Val Met His Glu Ala Leu His Asn His
305                 310                 315                 320
Tyr Thr Gln Lys Ser Ile Ser Lys Thr Pro Gly Lys
                325                 330
```

<210> SEQ ID NO 7
<211> LENGTH: 996
<212> TYPE: DNA
<213> ORGANISM: Artificial Sequence
<220> FEATURE:
<223> OTHER INFORMATION: Laboratory synthesis

<400> SEQUENCE: 7

| | | | | | |
|---|---|---|---|---|---|
| ttccctgacg | gcgagttcac | catgcagggc | tgccccgagt | gcaagctgaa | ggagaacaag | 60 |
| tacttctcca | gctgggcgc | cccatctac | cagtgcatgg | ctgctgctt | ctcccgggct | 120 |
| taccctaccc | ctgcccggtc | aagaagacc | atgctggtgc | caagaacat | acctccgag | 180 |
| gccacctgtt | gcgtggccaa | ggccttcacc | aaggccaccg | tgatgggcaa | cgccagggtg | 240 |
| gagaaccaca | ccgagtgcca | ctgcagcacc | tgctactacc | acaagtccgg | aggaggagga | 300 |
| tccggaggag | gcggctccgg | cggcggaggc | agcatctgtc | ctgcttgtga | gagcccggc | 360 |
| cctagcgtgt | ttatcttccc | ccccaagccc | aaggacaccc | tgatgatctc | caggaccccc | 420 |
| caggtcaccct | gtgtcgtggt | ggacgtgagc | caggagaacc | ctgaggtcca | gttttcctgg | 480 |
| tacgtggatg | gcgtggaggt | gcacaccgcc | cagaccaggc | caaggagga | acagttcaat | 540 |
| tccacctacc | gggtggtgag | cgtgctgcct | atccagcatc | aggactggct | gaacggaaag | 600 |
| gagtttaagt | gcaaggtcaa | caacaaggac | ctgcccgccc | ccatcaccag | gatcatcagc | 660 |
| aaagctaaag | gccagacccg | ggaaccccag | gtgtacaccc | tgcctcccca | cgctgaggag | 720 |
| ctgtccagga | gcaaggtgag | catcacatgc | ctggtcattg | gcttctaccc | tcccgacatc | 780 |
| gacgtcgaat | ggcagaggaa | tggccagccc | gaacccgagg | gaaactacag | gaccacccct | 840 |
| ccccagcagg | acgtggatgg | aacctatttt | ctgtactcca | agttctccgt | ggacaaggcc | 900 |

```
tcctggcagg gcggcggaat ttttcagtgc gccgtgatgc acgaggctct ccacaaccat    960
tacacccaga agtccatctc caagaccccc ggcaaa                              996
```

<210> SEQ ID NO 8
<211> LENGTH: 345
<212> TYPE: PRT
<213> ORGANISM: Artificial Sequence
<220> FEATURE:
<223> OTHER INFORMATION: Laboratory synthesis

<400> SEQUENCE: 8

```
Cys Glu Leu Thr Asn Ile Thr Ile Thr Val Glu Lys Glu Glu Cys Asn
1               5                   10                  15

Phe Cys Ile Ser Ile Asn Thr Thr Trp Cys Ala Gly Tyr Cys Tyr Thr
            20                  25                  30

Arg Asp Leu Val Tyr Lys Asp Pro Ala Arg Pro Asn Ile Gln Lys Thr
        35                  40                  45

Cys Thr Phe Lys Glu Leu Val Tyr Glu Thr Val Lys Val Pro Gly Cys
    50                  55                  60

Ala His His Ala Asp Ser Leu Tyr Thr Tyr Pro Val Ala Thr Glu Cys
65                  70                  75                  80

His Cys Gly Lys Cys Asp Ser Asp Ser Thr Asp Cys Thr Val Arg Gly
                85                  90                  95

Leu Gly Pro Ser Tyr Cys Ser Phe Ser Glu Met Lys Glu Gly Gly Gly
            100                 105                 110

Gly Ser Gly Gly Gly Ser Gly Gly Gly Ser Ile Cys Pro Ala
        115                 120                 125

Cys Glu Ser Pro Gly Pro Ser Val Phe Ile Phe Pro Pro Lys Pro Lys
    130                 135                 140

Asp Thr Leu Met Ile Ser Arg Thr Pro Gln Val Thr Cys Val Val Val
145                 150                 155                 160

Asp Val Ser Gln Glu Asn Pro Glu Val Gln Phe Ser Trp Tyr Val Asp
                165                 170                 175

Gly Val Glu Val His Thr Ala Gln Thr Arg Pro Lys Glu Glu Gln Phe
            180                 185                 190

Asn Ser Thr Tyr Arg Val Val Ser Val Leu Pro Ile Gln His Gln Asp
        195                 200                 205

Trp Leu Asn Gly Lys Glu Phe Lys Cys Lys Val Asn Asn Lys Asp Leu
    210                 215                 220

Pro Ala Pro Ile Thr Arg Ile Ile Ser Lys Ala Lys Gly Gln Thr Arg
225                 230                 235                 240

Glu Pro Gln Val Tyr Thr Leu Pro Pro His Ala Glu Glu Leu Ser Arg
                245                 250                 255

Ser Lys Val Ser Ile Thr Cys Leu Val Ile Gly Phe Tyr Pro Pro Asp
            260                 265                 270

Ile Asp Val Glu Trp Gln Arg Asn Gly Gln Pro Glu Pro Glu Gly Asn
        275                 280                 285

Tyr Arg Thr Thr Pro Pro Gln Gln Asp Val Asp Gly Thr Tyr Phe Leu
    290                 295                 300

Tyr Ser Lys Phe Ser Val Asp Lys Ala Ser Trp Gln Gly Gly Gly Ile
305                 310                 315                 320

Phe Gln Cys Ala Val Met His Glu Ala Leu His Asn His Tyr Thr Gln
                325                 330                 335

Lys Ser Ile Ser Lys Thr Pro Gly Lys
            340                 345
```

<210> SEQ ID NO 9
<211> LENGTH: 1035
<212> TYPE: DNA
<213> ORGANISM: Artificial Sequence
<220> FEATURE:
<223> OTHER INFORMATION: Laboratory synthesis

<400> SEQUENCE: 9

```
tgcgaactca caaacatcac catcaccgtg gaaaaggagg agtgcaactt ctgcatcagc    60
atcaacacca cctggtgcgc cggctattgc tatacaaggg atctggtcta caaggacccc   120
gccaggccca acatccagaa gacatgcacc ttcaaggagc tggtgtatga aaccgtgaag   180
gtccccggat gcgcccatca cgccgattcc ctgtacacct accccgtggc taccgagtgc   240
cattgcggca agtgcgactc cgactccacc gattgtacag tgagggggcct cggaccctcc   300
tactgctcct ttagcgagat gaaggaggga ggaggaggat ccggaggagg cggctccggc   360
ggcggaggca gcatctgtcc tgcttgtgag agccccggcc ctagcgtgtt tatcttcccc   420
cccaagccca aggacaccct gatgatctcc aggacccccc aggtcacctg tgtcgtggtg   480
gacgtgagcc aggagaaccc tgaggtccag ttttcctggt acgtggatgg cgtggaggtg   540
cacaccgccc agaccaggcc caaggaggaa cagttcaatt ccacctaccg ggtggtgagc   600
gtgctgccta tccagcatca ggactggctg aacggaaagg agtttaagtg caaggtcaac   660
aacaaggacc tgcccgcccc catcaccagg atcatcagca agctaaagg ccagacccgg   720
gaaccccagg tgtacaccct gcctccccac gctgaggagc tgtccaggag caaggtgagc   780
atcacatgcc tggtcattgg cttctaccct cccgacatcg acgtcgaatg gcagaggaat   840
ggccagcccg aacccgaggg aaactacagg accaccccctc cccagcagga cgtggatgga   900
acctattttc tgtactccaa gttctccgtg gacaaggcct cctggcaggg cggcggaatt   960
tttcagtgcg ccgtgatgca cgaggctctc cacaaccatt acacccagaa gtccatctcc  1020
aagacccccg gcaaa                                                    1035
```

<210> SEQ ID NO 10
<211> LENGTH: 5
<212> TYPE: PRT
<213> ORGANISM: Artificial Sequence
<220> FEATURE:
<223> OTHER INFORMATION: linker sequence
<220> FEATURE:
<221> NAME/KEY: REPEAT
<222> LOCATION: (1)..(5)
<223> OTHER INFORMATION: repeats two to five times, preferably three times

<400> SEQUENCE: 10

Gly Gly Gly Gly Ser
1               5

LONG-ACTING RECOMBINANT PORCINE FSH FUSION PROTEIN AND PREPARATION METHOD AND APPLICATION THEREOF

TECHNICAL FIELD

The present invention relates to the field of biomedicine and animal breeding technology, in particular to a long-acting recombinant porcine FSH fusion protein and a preparation method and application thereof.

BACKGROUND ART

Porcine follicle-stimulating hormone (pFSH) is a gonadotropin secreted by the porcine anterior pituitary, and which is formed by an α subunit and a β subunit that are non-covalently linked; wherein, the α subunit is highly conserved and identical to the α subunit of Porcine Luteinizing Hormone (pLH) and Porcine Thyroid Stimulating Hormone (pTSH); and the β subunit differs, which mainly determines the functional specificity of FSH. pFSH can promote the growth and maturation of sow endometrium, ovary and follicles; promote the synthesis and secretion of estrogen; and induce the development of boar seminiferous tubules and maintain spermatogenesis. pFSH is commonly used in the field of animal breeding for the synchronization of estrus, superovulation, embryo transplantation, and treatment of ovarian diseases in female animals. Studies show that the effect of porcine FSH for superovulation of cattle and sheep is better than that of FSH of cattle and sheep, and thus, pFSH is of great value in livestock production and economic animal breeding.

At present, related patents and articles report the expression of FSH fusion proteins, but most of them are related to the recombinant expression and application of a human FSH. The use of the human FSH in the field of animal breeding has also achieved some success. However, although humans and domestic animals belong to mammals, there are still large species differences in protein sequences (the human FSH and porcine FSH have a homology of 73% in term of the amino acid sequence of the α subunit, a homology of 93% in term of β subunit, and a homology of 73% in term of Fc fragment). If the human recombinant FSH is used in animals for a long time, the animal's immune system will recognize the human recombinant FSH and induce the production of antibodies (including neutralizing antibodies), which specifically bind to the receptor binding site of the animal FSH, thereby blocking the biological activity of the drug, and resulting in the lower and lower bioavailability of the human FSH in animals, which limits the application of the human FSH in animals, especially in economic animals such as pig, cattle and sheep that need to use FSH for a long time. This is one of the reasons why the currently marketed human recombinant FSH is not used in the field of animal breeding.

Currently, commercial FSH products on the market mainly include FSH extracted from porcine pituitary and pregnant mare serum gonadotropin (PMSG). Porcine pituitary FSH, such as Folltropin-V (Canada), has a short half-life (5 hours) and requires frequent administration, resulting in high cost of feeding and management for terminal customers. Furthermore, it is difficult to separate porcine FSH from LH when purified from porcine pituitary tissue, and the difficult purification and the low productivity greatly limit the practical applications of porcine FSH. PMSG is a glycoprotein hormone secreted by the chorioallantoic membrane cells of the placenta of an animal of genus *Equus*, has both FSH (high) and LH (low) activities, and has the effect of promoting the reproductive function of ovaries and testes of animals. In the field of animal breeding, PMSG is often used for inducing synchronization of estrus and superovulation of female animals, and treating reproductive disorders and ovarian insufficiency in female animals; promoting the development of seminiferous tubules and spermatogenesis in male animals. However, since PMSG molecules contain a relatively high amount of hexose and sialic acid, and have a long half-life in animals (120 h), when used in animals for superovulation, it is easy to cause various adverse effects in dams, such as ovarian cysts, early degradation of the embryo at the beginning of pregnancy. Furthermore, commercial PMSG is extracted and purified from the serum of pregnant horses; when used in other animals, antibodies will be produced, and PMSG has certain immunogenicity and cannot be used for a long time. In addition, PMSG is prepared by collecting serum from pregnant horses and this often causes abortion of pregnant horses and death of fetal horses due to excessive blood collection, which is inconformity with animal ethics.

Therefore, on the basis that human FSH is not suitable for animals, porcine pituitary FSH requires frequent administration, and PMSG is prone to cause adverse effects, there is a need for a long-acting animal-source FSH in the breeding field of animals, especially economic animals.

SUMMARY OF THE INVENTION

The purpose of the present invention is to provide a novel long-acting recombinant porcine FSH fusion protein and a preparation method and application thereof.

The concept of the present invention is as follows: Fc fusion protein technology is one of the most widely used and stable technologies in the development of long-acting protein drugs, and FSH is fused with Fc by genetic engineering technology to produce a novel recombinant protein FSH-Fc. Not only the high biological activity of FSH can be retained, but also a longer half-life can be obtained. At the same time, the obtained recombinant protein has high purity, relatively uniform quality, no LH and high safety factor. The use of mammalian expression systems, especially Chinese hamster ovary cells (CHO) for the expression of recombinant proteins, provides protein molecules that are closest to nature molecules in terms of molecular structure, physicochemical properties, and biological functions.

For the purposes of the present invention, the long-acting recombinant porcine FSH fusion proteins of the present invention comprise fusion proteins pFSH-Fc-1 and pFSH-Fc-2, wherein α subunit of the porcine FSH fusion protein pFSH-Fc-1 is directly or indirectly fused with the Fc fragment by means of a linking component, and β subunit of the porcine FSH fusion protein pFSH-Fc-1 binds with the α subunit by means of a Van der Waals force or a linking component; and β subunit of the porcine FSH fusion protein pFSH-Fc-2 is directly or indirectly fused with the Fc fragment by means of a linking component, and α subunit of the porcine FSH fusion protein pFSH-Fc-2 binds with the β subunit by means of a Van der Waals force or a linking component.

The porcine FSH fusion protein comprises two peptide chains conforming to the following equation: (pFSHβ:pFSHα-L-Fc)$_2$ or (pFSHα:pFSHβ-L-Fc)$_2$, wherein the pFSHβ refers to a β subunit of the porcine FSH with signal peptide removed; the colon represents the relationship that the porcine FSH β subunit and the α subunit are linked by means of a Van der Waals force; pFSHα refers to an α subunit of the porcine FSH with signal peptide removed; L represents the linking relationship between the pFSHα or pFSHβ subunit and the Fc fragment; Fc refers to the Fc fragment of the immunoglobulin, or a mutant thereof; the subscript 2 outside of the parenthesis represents that the porcine FSH fusion protein is a divalent homodimer.

The amino acid sequence of the pFSHα is represented by SEQ ID NO: 1, or the pFSHα is composed of an amino acid sequence having a homology of 90% or more with SEQ ID NO: 1 and an activity equivalent to that of SEQ ID NO: 1.

The amino acid sequence of the pFSHβ is represented by SEQ ID NO: 3, or the pFSHβ is composed of an amino acid sequence having a homology of 90% or more with SEQ ID NO: 3 and an activity equivalent to that of SEQ ID NO: 3.

The Fc comprises a hinge region as well as CH2 and CH3 regions of an immunoglobulin.

The immunoglobulin is derived from human, pig, cattle, sheep, horse or dog. Immunoglobulins are classified into IgG, IgM, IgA, IgD, and IgE, and each type of immunoglobulin includes various subtypes, such as IgG1, IgG2, IgG3, and IgG4.

The Fc mutant refers to a Fc variant comprising amino acid mutation at one or more sites in the Fc fragment, and includes a human IgG2 Fc variant comprising a human IgG2 hinge region, a CH2 region and a CH3 region, with a mutation Pro331Ser.

Preferably, the Fc is derived from a porcine immunoglobulin, i.e., pFc, and comprises the hinge region, CH2 and CH3 regions of the porcine immunoglobulin. The amino acid sequence of the pFc is represented by SEQ ID NO: 5, or the pFc is composed of an amino acid sequence having a homology of 80% or more with SEQ ID NO: 5 and an activity equivalent to that of SEQ ID NO: 5.

The pFSHα or pFSHβ subunit is linked to the Fc directly or by a linker, preferably by a linker.

Wherein, the linker is a flexible polypeptide consisting of 2 to 20 flexible amino acid selected from at least one of Gly, Ser, Ala and Thr;

Preferably, the linker is (Gly-Gly-Gly-Gly-Ser)$_n$ (SEQ ID NO: 10), wherein n is an integer between 2 and 5, more preferably n is 3.

Preferably, the pFSHα-L-Fc is: i) a protein constituted by the amino acid sequence as represented by SEQ ID No. 6; or ii) a protein derived from i), which is consisted of an amino acid sequence having a function equivalent to that of SEQ ID No. 6 and obtained from the amino acid sequence as represented by SEQ ID No. 6 by substitution, deletion and/or addition of one or more amino acids; or iii) a protein constituted by an amino acid sequence having a homology of 90% or more with the amino acid sequence as represented by SEQ ID No. 6 and having a function equivalent to that of SEQ ID No. 6.

Preferably, the pFSHβ-L-Fc is: iv) a protein constituted by the amino acid sequence as represented by SEQ ID No. 8; or v) a protein derived from iv), which is consisted of an amino acid sequence having a function equivalent to that of SEQ ID No. 8 and obtained from the amino acid sequence as represented by SEQ ID No. 8 by substitution, deletion and/or addition of one or more amino acids; or vi) a protein constituted by an amino acid sequence having a homology of 90% or more with the amino acid sequence as represented by SEQ ID No. 8 and having a function equivalent to SEQ ID No. 8.

The present invention also provides an expression cassette, expression vector, cloning vector, engineering bacteria or transgenic cell line, comprising a nucleic acid encoding the fusion protein described above.

The long-acting recombinant porcine FSH fusion protein of the present invention can be prepared as follows: artificially synthesizing genes encoding pFSHα, pFSHβ, pFSHα-L-Fc and pFSHβ-L-Fc, performing codon optimization, and cloning the optimized genes into eukaryotic expression vectors, respectively; simultaneously transforming the pFSHα recombinant vector and pFSHβ-L-Fc recombinant vector into eukaryotic cells, and expressing in eukaryotic cells, and isolating and purifying the target protein; simultaneously transforming the pFSHβ recombinant vector and pFSHα-L-Fc recombinant vector into eukaryotic cells, and expressing in eukaryotic cells, and isolating and purifying the target protein.

The eukaryotic expression vector includes, but is not limited to, pcDNA3.1, and the eukaryotic cells include, but are not limited to, 293 and CHO cells.

The present invention also provides the use of the above-mentioned long-acting recombinant porcine FSH fusion protein for the preparation of a medicament for promoting animal breeding (including synchronization of estrus, superovulation and the like) and for treating a reproductive-related disease in animals. Wherein the animal includes, but is not limited to, pig, cattle, sheep, horse or dog; preferably pig.

The present invention further provides a medicament for promoting animal breeding (including synchronization of estrus, superovulation and the like) and for treating a reproductive-related disease of an animal prepared from the above-mentioned long-acting recombinant porcine FSH fusion protein.

The invention also provides the use of the above-mentioned long-acting recombinant porcine FSH fusion protein in the field of animal breeding.

Modified proteins, including two fusion proteins pFSH-Fc-1, pFSH-Fc-2 or porcine FSH which has been glycosylated, PEGylated, acetylated or bound to BSA and the like are all within the scope of the present invention.

The engineered proteins, including two fusion proteins pFSH-Fc-1, pFSH-Fc-2 or fusion proteins that are constituted by fusing porcine FSH protein with porcine Fc or other proteins, without changes in the activity of porcine FSH protein, are all within the scope of the present invention.

Compared with the prior art, the present invention has the following advantages:

(I) The long-acting recombinant porcine FSH fusion protein and/or porcine FSH protein, and the derived proteins or modified proteins thereof provided by the present invention, have a half-life of about 60 h, which is higher than that of porcine pituitary FSH, but lower than that of PMSG. They do not require continuous injection, and do not cause adverse reactions due to excessive half-life in livestock; and they are not immunogenic for sows, and will not cause the production of drug-resistant antibodies.

(II) The long-acting recombinant porcine FSH fusion protein and/or porcine FSH protein, and the derived proteins or modified proteins thereof provided by the present invention, have an effective rate of 90% or more in promoting sow estrus, and an effective rate of 85% or more in the treatment of anestrus sows, and achieve an average ovulation rate of about 27 per pig, and an average litter size of about 13 per pig, and have better estrus and superovulation effect than those of PMSG, hFSH-hFc and pFSH-hFc.

(III) The long-acting recombinant porcine FSH fusion protein and/or porcine FSH protein, and the derived proteins or modified proteins thereof provided by the present invention, can also improve the estrus rate of cattle and sheep, and promote the superovulation effect: the number of embryos per cow is about 8.0, and the number of available embryos per cow is about 6.1, which are respectively higher than those of PMSG, hFSH-hFc and pFSH-hFc; and have an effective rate of 90% or more in promoting ewes estrus, which is also better than that of PMSG, hFSH-hFc and pFSH-hFc.

(IV) The long-acting recombinant porcine FSH fusion protein and/or porcine FSH protein, and the derived proteins or modified proteins thereof provided by the present invention, can effectively provide a safe and effective drug for promoting the reproduction rate of animals, especially economic animals.

(V) When applying to the field of animal breeding, the long-acting recombinant porcine FSH fusion protein and/or porcine FSH protein, and the derived proteins or modified proteins thereof have lower immunogenicity and higher biological activity as compared with human FSH, have higher purity and longer half-life as compared with natural porcine pituitary FSH, and have fewer adverse side effects and lower immunogenicity as compared with PMSG.

(VI) The long-acting recombinant porcine FSH fusion protein provided by the present invention can effectively prolong the half-life of porcine FSH, reduce the number of administrations, reduce the immunogenicity, and increase the estrus rate and the ovulation number of pig, cattle, sheep and the like, and does not cause adverse reactions to animals, and can replace porcine pituitary FSH and PMSG in the field of animal breeding.

SPECIFIC MODES FOR CARRYING OUT THE EMBODIMENTS

The following Examples are intended to illustrate the present invention but are not intended to limit the scope of the present invention. Unless otherwise indicated, the Examples are based on routine experimental conditions, such as Sambrook J & Russell D W, Molecular Cloning: a Laboratory Manual, 2001, or according to the conditions suggested by the manufacturer's instructions.

The hFSH-hFc and pFSH-hFc described in the following Examples are both obtained by linking β subunits to hFc, and the construction method is the same as that of pFSH-Fc-2, and comprises: the gene sequences of human FSHα, human FSHβ, and human Fc were found after search, after codon optimization, the hFSHα, hFSHβ-L-hFc, pFSHα, and pFSHβ-L-hFc genes were artificially synthesized, and the hFSHa and hFSHβ-L-hFc, pFSHα and pFSHβ-L-hFc recombinant plasmids were transferred into 293 cells by transient transfection for expression, and purification was performed to obtain hFSH-hFc and pFSH-hFc.

Example 1: Preparation of pFSH-Fc-1 and pFSH-Fc-2 Proteins

The GeneBank was searched for gene sequences of porcine FSHα (GenBank NM-214446.1), porcine FSHβ (GenBank NM-213875.1) and porcine Fc (GenBank BAE20056). Codon optimization was performed. The nucleotide sequence of pFSHα is represented by SEQ ID NO: 2; the nucleotide sequence of pFSHβ is represented by SEQ ID NO: 4; the sequence of pFSHα-L-pFc is represented by SEQ ID NO: 7; and the sequence of pFSHr3-L-pFc is represented by SEQ ID NO: 9.

The artificially synthesized pFSHα, pFSHβ, pFSHα-L-pFc and pFSHβ-L-pFc genes were cloned into the vector pcDNA3.1, respectively. The recombinant vectors of pFSHβ and pFSHα-L-pFc, pFSHα and pFSHβ-L-pFc were respectively electrotransferred into 293 cells to express pFSH-Fc-1 and pFSH-Fc-2, and the proteins obtained by transient transfection and expression were purified and verified for the activity. After the activity was confirmed, the recombinant vectors of pFSHβ and pFSHα-L-pFc, pFSHα and pFSHβ-L-pFc were linearized and then electrotransferred into CHO cells to obtain stable cell lines of pFSH-Fc-1 and pFSH-Fc-2.

Figure 1:
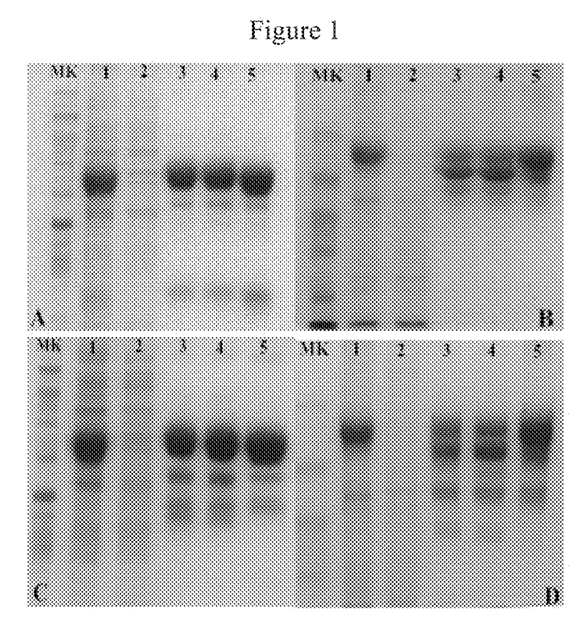
FIG. 1 is a diagram showing the SDS-PAGE electrophoresis of pFSH-Fc-1 and pFSH-Fc-2 in Example 1 of the present invention. Wherein, A and C are denatured electropherograms of pFSH-Fc-1 and pFSH-Fc-2, respectively; B and D are non-denatured electropherograms of pFSH-Fc-1 and pFSH-Fc-2, respectively. MK: Protein Marker; 1: Clarified fermentation broth; 2: flow-through solution from Protein A chromatography; 3: solution collected from Protein A chromatography; 4: solution collected from Capto S chromatography; and 5: solution collected from Capto Q chromatography. The structural formula of pFSH-Fc-1 is (pFSHβ:pFSHα-L-Fc)2, and the structural formula of pFSH-Fc-2 is (pFSHα:pFSHβ-L-Fc)$_2$.

The stable cells of pFSH-Fc-1 and pFSH-Fc-2 were subjected to fermentation cultivation in a fermentor, and the fermentation broth was subjected to filtration to remove cells and cell debris using two-stage deep bed filtration membrane package, and then filtered through a 0.22 μm filter membrane to obtain clarified fermentation broth. The fermentation broth was firstly purified by Protein A affinity chromatography (MabSelect SuRe™, GE Healthcare): firstly, equilibrated to the baseline with an equilibration solution (50 mM glycine, 0.15 M NaCl, pH 7.2) and then eluted with an eluent (50 mM glycine, pH 3.0), and the eluate was collected. The solution collected from Protein A chromatography was further purified by Capto S cation exchange column (GE Healthcare) chromatography: the collected solution was adjusted to a pH of 6.5 with 1 M NaOH, the conductivity thereof was adjusted to 4.5 to 5.0 ms/cm with water, the collected solution was equilibrated with an equilibration solution (50 mM glycine, pH 6.5), loaded, and the flow-through effluent was collected. The solution collected from Capto S chromatography was finely purified by Capto Q anion exchange column (GE Healthcare) chromatography: the collected solution was adjusted to a pH of 8 with 1 M NaOH, and equilibrated to baseline with an equilibration solution (50 mM glycine pH 8.0), followed by eluting with eluent (50 mM glycine, 1 M KCl, pH 8.0), and the purified protein was collected. The purified protein of interest was subjected to SDS-PAGE gel electrophoresis (FIG. 1).

Example 2: Activity Assay of pFSH-Fc-1 and pFSH-Fc-2 Proteins

Figure 2:
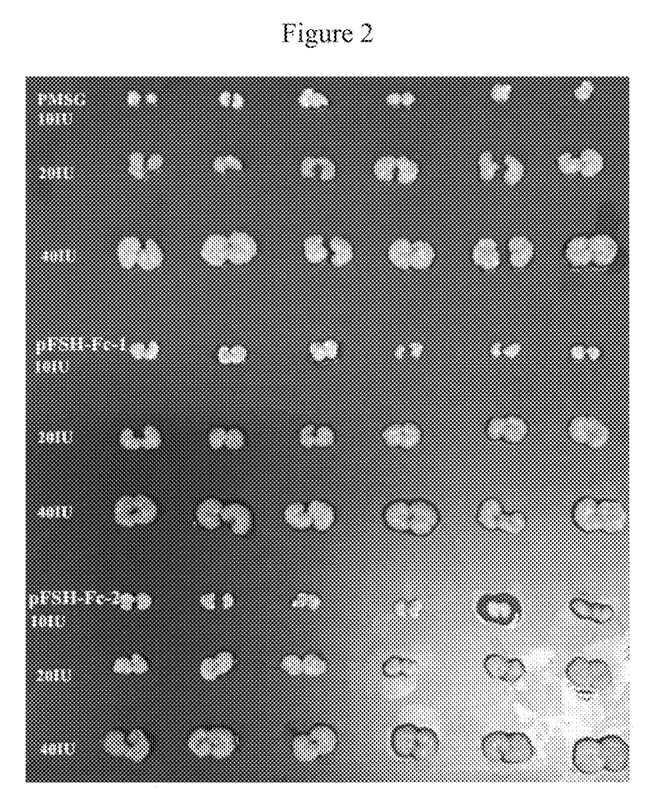
FIG. 2 is a diagram showing the rat ovary of the pFSH-Fc-1, pFSH-Fc-2 and PMSG groups in Example 2 of the present invention. Wherein, 10 IU, 20 IU and 40 IU represent that the rats in the pFSH-Fc-1, pFSH-Fc-2, and PMSG groups were injected with the corresponding drugs in amounts of 10 IU, 20 IU and 40 IU, respectively.

The activities of pFSH-Fc-1 and pFSH-Fc-2 were measured using a rat ovarian weight gain method (Steelman- Pohley method). The product of the present invention is intended to be used in place of PMSG in the field of animal breeding. Therefore, the activity of the sample was determined according to the *Pharmacopoeia of China* 2015 Edition "Serum Gonadotropin Bioassay", with PMSG as a standard. The specific process for implementation was as follows: pFSH-Fc-1 (with an estimated value of specific activity of 10000 U/mg), pFSH-Fc-2 (with an estimated value of specific activity of 10000 U/mg) and PMSG were formulated into three doses of 40 IU (high), 20 IU (medium) and 10 IU (low), respectively. Female SD (Sprague Dawley) rats of 21-23 day-old, weighted 40-55 g were randomly divided into 9 groups, 6 in each group. Each rat was subcutaneously injected with 0.5 ml of the corresponding drug. After 6 days, the rats were sacrificed, weighed, and dissected, the ovaries were removed, and weighed and the ovary weight was converted into ovary weight per 100 g body weight (FIG. 2). The specific activity of pFSH-Fc-1 was calculated to be about 9600 U/mg using the software of National Institutes for Food and Drug Control, "Pharmacopoeia Bioassay Statistics BS2000", and the specific activity of pFSH-Fc-2 was about 10700 U/mg.

Example 3: Pharmacokinetic Study of pFSH-Fc-1 and pFSH-Fc-2 Proteins

Ten SD female rats of about 40 g were randomly divided into two groups: pFSH-Fc-1 group and pFSH-Fc-2 group. The corresponding drug was subcutaneously injected at 20 IU/kg body weight, 100 μl of blood was sampled at 0, 1, 2, 4, 8, 12, 24, 48, 72, 96, 120, and 144 h after administration, respectively, centrifuged at 3000 rpm, and the serum was taken and stored at −80° C. for cryopreservation. The contents of pFSH-Fc-1 and pFSH-Fc-2 in the serum were measured using an FSH ELISA kit, and each blood sample was analyzed in triplicate. The half-life of pFSH-Fc-1 was calculated to be 57.2 h using Pksolver software, and the half-life of pFSH-Fc-2 was 63.4 h, both of which were higher than that of natural porcine FSH, and lower than that of PMSG.

Figure 3:
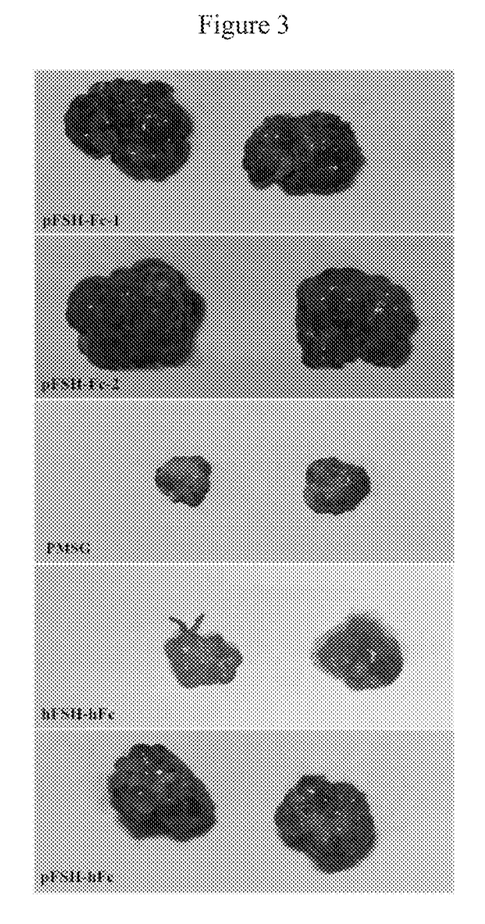
FIG. 3 is a diagram showing the ovary of No. 1 superovulated primiparous sows of pFSH-Fc-1, pFSH-Fc-2, PMSG, hFSH-hFc and pFSH-hFc groups in Example 4 of the present invention.

Example 4: Use of pFSH-Fc-1 and pFSH-Fc-2 Proteins in Promoting Synchronization of Estrus and Superovulation in Primiparous and Multiparous Sows 100 primiparous Yorkshire sows and multiparous Yorkshire sows without estrus 2 weeks after weaning, weighed 85-100 kg with the same variety and similar signs were selected, respectively. They were randomly divided into 5 groups: pFSH-Fc-1, pFSH-Fc-2, PMSG, hFSH-hFc and pFSH-hFc groups; each group was further divided into primiparous sow group and multiparous sow group. 1000 IU of the corresponding drugs were injected into the neck muscles at the back of ear of the donor pigs in each group, and 500 IU of HCG was injected 72 hours later. The estrus of each group of sows was observed after 5 days. Except for the oestrous No. 1 Yorkshire sow in the primiparous sow group was slaughtered and taken ovary for photographing, the oestrous sows of other groups were bred with the boars of the same variety for 3 times at intervals of 12 h each time. 36 hours after the first breeding, the donor pigs were subjected to surgery for ovums, and the number of ovums ovulated was counted (FIG. 3).

The results were shown in Table 1, The donor pigs in each group had good estrus, and the estrus rate of the primiparous and multiparous sows in the pFSH-Fc-1 group were 90% and 95%, respectively, which were higher than those of the PMSG group (60% and 65%), the hFSH-hFc group (65% and 70%) and the pFSH-hFc group (80% and 85%), and were significantly different from those of the PMSG group and the hFSH-hFc group ($P<0.05$). The estrus rates of the primiparous and multiparous sows in the pFSH-Fc-2 group were 100%, and were significantly different from those of the PMSG group and the hFSH-hFc group ($P<0.01$).

The number of ovums ovulated in each group of sows was higher than that in normal natural oestrous sows (8 to 14/pig), and the average number of ovums ovulated per pig of the primiparous and multiparous sows in the pFSH-Fc-1 group was 27.7 and 27.5, respectively, which were higher than those of the PMSG group (19.8 and 20.2), the hFSH-hFc group (22.1 and 21.6), and the pFSH-hFc group (25.7 and 26.2), and were significantly different from those of the PMSG group and the hFSH-hFc group ($P<0.05$). The average number of ovums ovulated per pig of the primiparous and multiparous sows in the pFSH-Fc-2 group was 29.9 and 29.1, respectively, which were higher than that of the PMSG group, the hFSH-hFc group and the pFSH-hFc group, and were significantly different from those of the PMSG group and the hFSH-hFc group ($P<0.05$).

TABLE 1

Comparison of pFSH-Fc-1, pFSH-Fc-2, PMSG, hFSH-hFc and pFSH-hFc on synchronization of estrus and superovulation in primiparous and multiparous sows

| | pFSH-Fc-1 group | | pFSH-Fc-2 group | | PMSG group | |
|---|---|---|---|---|---|---|
| Item | primiparous sows | multiparous sows | primiparous sows | multiparous sows | primiparous sows | multiparous sows |
| Number of sows tested | 20 | 20 | 20 | 20 | 20 | 20 |
| Number of oestrous sows | 18 | 19 | 20 | 20 | 12 | 13 |
| Estrus rate | 90%$^{ACe}$ | 95%$^{BDf}$ | 100%$^{AACCe}$ | 100%$^{BBDDf}$ | 60%$^{a}$ | 65%$^{b}$ |
| Number of fertilized sows | 11 | 11 | 11 | 11 | 11 | 11 |
| Number of ovums ovulated per pig | 27.7 ± 2.10$^{GJk}$ | 27.5 ± 2.11$^{HJl}$ | 29.9 ± 2.66$^{GJk}$ | 29.1 ± 2.30$^{HJl}$ | 19.8 ± 2.04$^{g}$ | 20.2 ± 2.13$^{h}$ |

TABLE 1-continued

Comparison of pFSH-Fc-1, pFSH-Fc-2, PMSG, hFSH-hFc and pFSH-hFc on synchronization of estrus and superovulation in primiparous and multiparous sows

|  | | pFSH-hFc group | | pFSH-hFc group | |
| --- | --- | --- | --- | --- | --- |
| Item | | primiparous sows | multiparous sows | primiparous sows | multiparous sows |
| | Number of sows tested | 20 | 20 | 20 | 20 |
| | Number of oestrous sows | 13 | 14 | 16 | 17 |
| | Estrus rate | 65%$^c$ | 70%$^d$ | 80%$^e$ | 85%$^f$ |
| | Number of fertilized sows | 11 | 11 | 11 | 11 |
| | Number of ovums ovulated per pig | 22.1 ± 2.34$^i$ | 21.6 ± 1.91$^j$ | 25.7 ± 2.33$^k$ | 26.2 ± 2.23$^l$ |

Note:
The different capital and lower-case letters of the series superscript on the same line showed significant difference (P < 0.05), different double capital and lower-case letters showed highly significant difference (P < 0.01), and the same letter showed non-significant difference (P > 0.05).

Example 5: Application of pFSH-Fc-1 and pFSH-Fc-2 Proteins in Increasing Litter Size of SOWS 50 primiparous Yorkshire sows with the same variety and similar signs were selected. They were divided into 5 groups: pFSH-Fc-1, pFSH-Fc-2, PMSG, hFSH-hFc and pFSH-hFc groups, each group of sows were injected with drugs according to the method of Example 4. During estrus, the oestrous sows were bred with the boars of the same variety for 3 times at intervals of 12 h each time. The litter size of each group of sows was recorded in detail.

The results were shown in Table 2, the total number of litter sizes of sows in the pFSH-Fc-1 and pFSH-Fc-2 groups (123 and 125) were higher than that of the PMSG group (65), the hFSH-hFc group (68) and the pFSH-hFc group (99), and were significantly different from those of the PMSG and the hFSH-hFc groups (P<0.05). The average number of litter sizes per birth of the pFSH-Fc-1 and pFSH-Fc-2 groups (13.7 and 13.9) were also higher than that of the PMSG group (10.1), the hFSH-hFc group (10.5), and the pFSH-hFc group (12.4).

TABLE 2

Comparison of pFSH-Fc-1, pFSH-Fc-2, PMSG, hFSH-hFc and pFSH-hFc on litter sizes of primiparous sows

| Groups | Number of sows tested | Number of farrowing sows | Total number of litter sizes | Average number of litter sizes per birth |
| --- | --- | --- | --- | --- |
| pFSH-Fc-1 group | 10 | 9 | 123$^{ABc}$ | 13.7 ± 1.25 |
| pFSH-Fc-2 group | 10 | 9 | 125$^{ABc}$ | 13.9 ± 1.19 |
| PMSG group | 10 | 6 | 65$^a$ | 10.1 ± 1.34 |
| hFSH-hFc group | 10 | 6 | 68$^b$ | 10.5 ± 1.38 |
| pFSH-hFc group | 10 | 8 | 99$^c$ | 12.4 ± 1.27 |

Note:
The different capital and lower-case letters of the series superscript on the same column showed significant difference (P < 0.05), and the same letter showed non-significant difference (P > 0.05).

Example 6: Application of pFSH-Fc-1 and pFSH-Fc-2 Proteins in the Treatment of Anestrus Sows 100 anestrus Yorkshire sows without estrus for more than 21 days after weaning were randomly divided into 5 groups: pFSH-Fc-1, pFSH-Fc-2, PMSG, hFSH-hFc and pFSH-hFc groups. 1000 IU of the corresponding drugs were respectively injected into the neck muscles at the back of ear of the donor pigs in each group, and 500 IU of HCG was injected 72 hours later. The estrus characteristics of sows were observed: such as redness and mucus in the vulva; and standing reflex occurs when the back is pressed. The oestrous sows were bred with boars according to Examples 4 and 5, and the impregnation conditions were recorded.

The results were shown in Table 3. The anestrus sows were sensitive to drug reactions, and the estrus rates of the sows in the pFSH-Fc-1 and pFSH-Fc-2 groups (85% and 90%) were higher than those of the PMSG group (55%), the hFSH-hFc group (65%) and the pFSH-hFc group (75%), and were significantly different from that of the PMSG group (P<0.05). The pregnancy rates of the sows in the pFSH-Fc-1 and pFSH-Fc-2 groups (88.2% and 88.9%) were also higher than those of the PMSG group (63.6%), the hFSH-hFc group (61.5%) and the pFSH-hFc group (73.3%), and the difference was not significant (P>0.05).

TABLE 3

Comparison of pFSH-Fc-1, pFSH-Fc-2, PMSG, hFSH-hFc and pFSH-hFc in inducing the estrus of the anestrus sows

| Groups | Number of sows tested | Number of oestrous sows | Estrus rates | Pregnancy rates |
| --- | --- | --- | --- | --- |
| pFSH-Fc-1 group | 20 | 17 | 85%$^{Abc}$ (17/20) | 88.2%$^{def}$ (15/17) |
| pFSH-Fc-2 group | 20 | 18 | 90%$^{Abc}$ (18/20) | 88.9%$^{def}$ (16/18) |
| PMSG group | 20 | 11 | 55%$^a$ (11/20) | 63.6%$^d$ (7/11) |
| hFSH-hFc group | 20 | 13 | 65%$^b$ (13/20) | 61.5%$^e$ (8/13) |
| pFSH-hFc group | 20 | 15 | 75%$^c$ (15/20) | 73.3%$^f$ (11/15) |

Note:
The different capital and lower-case letters of the series superscript on the same column showed significant difference (P < 0.05), and the same letter showed non-significant difference (P > 0.05).

Example 7: Application of pFSH-Fc-1 and pFSH-Fc-2 Proteins in Promoting Superovulation of Cows 50 3-6 years old, healthy, disease-free Holstein cows were randomly divided into pFSH-Fc-1, pFSH-Fc-2, PMSG, hFSH-hFc, and pFSH-hFc groups. Each group of cows was fed 1 kg of concentrate feed based on the original feeding, at the same time, VA, VD and VE were intramuscularly injected. Each donor cow was implanted with progesterone vaginal plug CIDR (containing progesterone 1.56 g/vaginal plug). The day of plugging was recorded as Day 0, each group of donor cows was intramuscularly injected with 1000 IU of the corresponding drug (Day 5), and 0.5 mg of cloprostenol (PG) was injected, and then the plug was removed (Day 10), and the estrus was observed, the mounting of the bull accepted by donor cow shall prevail. The first insemination was performed 12 h after standing estrus, the second insemination was performed 24 h after standing estrus. Embryos were collected on Day 16 by non-surgically washing, and the number of embryos was counted.

The results were shown in Table 4, the superovulation effects of donor cows in each administration group were remarkable (naturally, one cow generates only one embryo at a time), and the average numbers of embryos per cow in the pFSH-Fc-1 group and the pFSH-Fc-2 group (7.9 and 8.7) were higher than that of the PMSG group (5.7), the hFSH-hFc group (6.1), and the pFSH-hFc group (7.3), and were significantly different from those of the PMSG group and the hFSH-hFc group (P<0.05). The average numbers of available embryos per cow in the pFSH-Fc-1 and the pFSH-Fc-2 groups (6.1 and 7.4) were higher than those in the PMSG group (3.5), the hFSH-hFc group (3.9) and the pFSH-hFc group (5.7), and were significantly different from those of the PMSG group and the hFSH-hFc group (P<0.05). The average numbers of unavailable embryos per cow in the pFSH-Fc-1 and pFSH-Fc-2 groups (1.8 and 1.3) were lower than those in the PMSG group (2.2) and the hFSH-hFc group (2.2), and that in the pFSH-Fc-2 group was less than that in the pFSH-hFc group (1.6), and the difference between the pFSH-Fc-2 group and the PMFG group as well as the hFSH-hFc group was significant (P<0.05).

TABLE 4

Comparison of pFSH-Fc-1, pFSH-Fc-2, PMSG, hFSH-hFc and pFSH-hFc on superovulation of Holstein cows

| Groups | Average numbers of embryos per cow | Average numbers of available embryos per cow | Average numbers of unavailable embryos per cow |
|---|---|---|---|
| pFSH-Fc-1 group | 7.9 ± 0.70$^{ABc}$ | 6.1 ± 0.94$^{DEf}$ | 1.8 ± 0.40$^{ghi}$ |
| pFSH-Fc-2 group | 8.7 ± 0.78$^{ABc}$ | 7.4 ± 0.91$^{DEf}$ | 1.3 ± 0.46$^{GHi}$ |
| PMSG group | 5.7 ± 0.64$^{a}$ | 3.5 ± 0.81$^{d}$ | 2.2 ± 0.60$^{g}$ |
| hFSH-hFc group | 6.1 ± 0.70$^{b}$ | 3.9 ± 0.70$^{e}$ | 2.2 ± 0.87$^{h}$ |
| pFSH-hFc group | 7.3 ± 0.95$^{c}$ | 5.7 ± 0.95$^{f}$ | 1.6 ± 0.70$^{i}$ |

Note:
The different capital and lower-case letters of the series superscript on the same column showed significant difference (P < 0.05), and the same letter showed non-significant difference (P > 0.05).

Example 8 Application of pFSH-Fc-1 and pFSH-Fc-2 Proteins in Promoting Synchronization of Estrus in Female Goats 75 1.5-3 years old, weighed 30-45 kg, healthy, disease-free goats were randomly divided into pFSH-Fc-1, pFSH-Fc-2, PMSG, hFSH-hFc and pFSH-hFc groups. The progesterone vaginal plug was implanted on the donor goat at any day in the estrus cycle and the day was recorded as Day 0. Each donor goat was intramuscularly injected with 300 IU of the corresponding drug (Day 10), and then the plug was removed (Day 12). The estrus performance of the female goat was observed, and a teaser goat was used to judge whether the female goat was oestrous. The situations of redness and mucus in the vulva of the female goat and the acceptance of mounting were considered as estrus, and the estrus rate was calculated.

The results were shown in Table 5, the estrus of female goats in each group was obvious, and the estrus rates of female goats in the pFSH-Fc-1 group and the pFSH-Fc-2 group were both 93.3%, which were higher than those of the PMSG group (60%), the hFSH-hFc group (73.3%) and the pFSH-hFc group (80.0%), and were significantly different from that of the PMSG group (P<0.05).

TABLE 5

Comparison of pFSH-Fc-1, pFSH-Fc-2, PMSG, hFSH-hFc and pFSH-hFc on estrus of female goats

| Groups | Number of female goats tested | Number of oestrous female goats | Estrus rates |
|---|---|---|---|
| pFSH-Fc-1 group | 15 | 14 | 93.3%$^{Abc}$ (14/15) |
| pFSH-Fc-2 group | 15 | 14 | 93.3%$^{Abc}$ (14/15) |
| PMSG group | 15 | 9 | 60.0%$^{a}$ (9/15) |
| hFSH-hFc group | 15 | 11 | 73.3%$^{b}$ (11/15) |
| pFSH-hFc group | 15 | 12 | 80.0%$^{c}$ (12/15) |

Note:
The different capital and lower-case letters of the series superscript on the same column showed significant difference (P < 0.05), and the same letter showed non-significant difference (P > 0.05).

Example 9: Detection of Antigenic Immunity of pFSH-Fc-1 and pFSH-Fc-2 Proteins

The antigenic immunities of the pFSH-Fc-1 and pFSH-Fc-2 proteins were detected by detecting the anti-drug antibody (ADA) of the drug in the serum of the sample by using the Bridging-ELISA method. 40 primiparous Yorkshire sows were selected and divided into 4 groups: pFSH-Fc-1 group, pFSH-Fc-2 group, hFSH-hFc group and pFSH-hFc group. 1000 IU of the drugs were injected into the neck muscle at the back of ear of each donor pig, and administered once every three days for a total of 5 weeks (13 times of administration), and the day for the first administration was recorded as Day 0. Blood was collected at the following times: before the first administration (Day −2), before the third administration (Day 6), before the fifth administration (Day 12), and before the sixth to last administration (Day 15, 18, 21, 24, 27, 30, 33 and 36), and the third day after the last administration (Day 39). The blood was centrifuged, the serum was collected, and the OD$_{490nm}$ value of ADA in the serum was detected in the ELISA plate coated with pFSH-Fc-1, pFSH-Fc-2, hFSH-hFc or pFSH-hFc, respectively. Positive control samples were prepared with anti-pFSH-Fc-1, anti-pFSH-Fc-2, anti-hFSH-hFc or anti-pFSH-hFc rabbit monoclonal antibody diluted with 100% mixed pig serum, respectively; and negative control (N) samples were prepared with serum of a primiparous Yorkshire sow injected with the same amount of PBS buffer. The threshold value (SCP) was used as the judgment value to distinguish whether the test sample was positive or negative. The SCP was calculated to be 1.15 by using JMP® statistical analysis, that is, SCP 1.15 was judged to be positive, and the sample contained ADA; otherwise it was negative and the sample did not contain ADA.

The results were shown in Table 6, the SCPs of the donor pig samples in pFSH-Fc-1 group and pFSH-Fc-2 group were all less than 1.15, and no ADA was detected, indicating that no anti-drug antibody was generated in the Yorkshire sows injected with 1000 IU of pFSH-Fc-1 or pFSH-Fc-2. In the hFSH-hFc group, the SCPs in the serum samples of Nos. 1, 2, 4, 7 and 9 sows were greater than 1.15 on Day 27 and after Day 27 (first detected on Day 27, and last detected on Day 39), and the SCPs in the serum samples of other sows were greater than 1.15 on Day 30 and after Day 30 (first detected on Day 30, and last detected on Day 39), indicating that ADA was detected in all sows in the hFSH-hFc group, i.e., a positive rate of 100%. In the pFSH-hFc group, the SCPs in the serum samples of Nos. 2, 3, 6, 7 and 9 sows were greater than 1.15 on Day 30 and after Day 30 (first detected on Day 30, and last detected on Day 39), the SCPs in the serum samples of Nos. 1, 5, and 8 sows were greater than 1.15 on Day 36 and after Day 36 (first detected on Day 36, and last detected on Day 39), and the SCPs in all serum samples of Nos. 4 and 10 sows were less than 1.15, indicating that ADA was detected in 8 sows in the pFSH-hFc group, i.e., a positive rate of 80%. The above-mentioned results indicate that the Yorkshire sows injected with 1000 IU of hFSH-hFc or pFSH-hFc generate anti-drug antibody.

TABLE 6

Detection of antigenic immunity of pFSH-Fc-1, pFSH-Fc-2, hFSH-hFc and pFSH-hFc to Yorkshire sows

|  | Groups | | | |
| --- | --- | --- | --- | --- |
|  | pFSH-Fc-1 | pFSH-Fc-2 | hFSH-hFc | pFSH-hFC |
| Administration dosage | 1000IU/pig | 1000IU/pig | 1000IU/pig | 1000IU/pig |
| Time for the first detection | — | — | Day 27 | Day 30 |
| Time for the last detection | — | — | Day 39 | Day 39 |
| Number of individuals in each group | 10 | 10 | 10 | 10 |
| Number of positive individuals | 0 | 0 | 10 | 8 |
| Individual positive rate | 0% | 0% | 100% | 80% |

Although the present invention is described in detail using general description and specific embodiments hereinbefore, it is obvious to a person skilled in the art that some modifications or improvements can be made based on the present invention. Hence all these modifications or improvements made on the basis of not deviating from the spirit of the present invention fall into the protection scope claimed in the present invention.

INDUSTRIAL APPLICABILITY

The present invention provides two long-acting recombinant porcine FSH (follicle-stimulating hormone) fusion proteins, comprising pFSH-Fc-1 and pFSH-Fc-2. α subunit/β subunit is directly or indirectly fused with a Fc fragment by means of a linking component; the β subunit/α subunit binds with the α subunit/β subunit by means of a Van der Waals force or the linking component. The porcine FSH fusion proteins can be prepared by an eukaryotic expression system based on a gene engineering technology. The two porcine FSH fusion proteins provided by the present invention have a good medicinal effect and have a longer half-life period as compared with that of a natural porcine FSH; do not generate an undesirable effect in animals, do not have immunogenicity in the sow, do not cause anti-drug antibody, and can replace pregnant mare serum gonadotropin (PMSG) used in animal breeding production, can effectively promote the reproduction rate of animals, especially economic animals, and have good economic value and application prospects.

COMPUTER READABLE SEQUENCE LISTING

The material contained in the ASCII text file entitled, "CNKH27US_AmendedSequence_Listing4" created on Jul. 16, 2021, having a size of 14 kB is hereby incorporated by reference herein in its entirety.

---

What is claimed is:

1. A long-acting recombinant porcine FSH fusion protein pFSH-Fc-1;

wherein the pFSH-Fc-1 comprises two peptide chains and conforms to the equation (pFSHβ:pFSHα-L-Fc)$_2$, the pFSHβ refers to a β subunit of the porcine FSH with a signal peptide removed; the colon represents the relationship that the porcine FSH β subunit and the porcine FSH α subunit are linked by a Van der Waals force; pFSHα refers to an α subunit of the porcine FSH with a signal peptide removed; L represents the linking relationship between the pFSHα subunit and the Fc fragment; Fc refers to an Fc fragment of an immunoglobulin; and the subscript 2 outside of the parenthesis represents that pFSH-Fc-1 is a divalent homodimer, and the amino acid sequence of the pFSHα-L-Fc is shown in SEQ ID NO: 6, and the amino acid sequence of the pFSHβ is shown in SEQ ID NO: 3.

2. An expression cassette or an expression vector, comprising a nucleic acid encoding the recombinant porcine FSH fusion protein according to claim 1.

3. A CHO cell for expressing of a fusion protein, the cell comprising the expression vector of claim 2.

4. A method for synchronizing estrus and superovulation in an animal comprising the step of administering at least one of recombinant porcine FSH fusion proteins according to claim 1, wherein the animal is a pig, a cow or a goat.

5. The method of claim 4, wherein the animal is a pig.

6. A method for treating anestrus in a pig by administering a fusion protein according to claim 1.

7. A cloning vector comprising a nucleic acid encoding a fusion protein according to claim 1.

8. A long-acting recombinant porcine FSH fusion protein pFSH-Fc-2 comprising two peptide chains and conforms to the equation: (pFSHα:pFSHβ-L-Fc)$_2$, wherein the pFSHβ refers to a β subunit of the porcine FSH with a signal peptide removed; the colon represents the relationship that the porcine FSH β subunit and the porcine FSH α subunit are linked by a Van der Waals force; pFSHα refers to an α subunit of the porcine FSH with a signal peptide removed; L represents the linking relationship between the pFSHβ subunit and the Fc fragment; Fc refers to an Fc fragment of an immunoglobulin; and the subscript 2 outside of the parenthesis represents that FSH-Fc-2 is a divalent homodimer, and the amino acid sequence of the pFSHβ-L-Fc is shown in SEQ ID NO: 8, and the amino acid sequence of the pFSHα is shown in SEQ ID NO:1.

9. An expression cassette or an expression vector, comprising a nucleic acid encoding the recombinant porcine FSH fusion protein according to claim 8.

10. A CHO cell for expressing a fusion protein, the cell comprising the expression vector of claim 9.

11. A cloning vector comprising a nucleic acid encoding a fusion protein according to claim 8.

12. A method for synchronizing estrus and superovulation in an animal comprising the step of administering at least one of recombinant porcine FSH fusion proteins according to claim 8, wherein the animal is a pig, a cow or a goat.

13. A method for treating anestrus in a pig by administering a fusion protein according to claim 8.

14. A method for preparing a recombinant porcine FSH fusion protein selected from the group consisting of:
(a) a long-acting recombinant porcine FSH fusion protein pFSH-Fc-1; wherein the pFSH-Fc-1 comprises two peptide chains and conforms to the equation (pFSHβ: pFSHα-L-Fc)$_2$, the pFSHβ refers to a β subunit of the porcine FSH with a signal peptide removed; the colon represents the relationship that the porcine FSH β subunit and the porcine FSH α subunit are linked by a Van der Waals force; pFSHα refers to an α subunit of the porcine FSH with a signal peptide removed; L represents the linking relationship between the pFSHα subunit and the Fc fragment; Fc refers to a Fc fragment of an immunoglobulin; and the subscript 2 outside of the parenthesis represents that pFSH-Fc-1 is a divalent homodimer, and the amino acid sequence of the pFSHα-L-Fc is shown in SEQ ID NO: 6, and the amino acid sequence of the pFSHβ is shown in SEQ ID NO: 3; and (b) a long-acting recombinant porcine FSH fusion protein pFSH-Fc 2 wherein the pFSH-Fc-2 comprises two peptide chains and conforms to the equation (pFSHα: pFSHβ-L-Fc)$_2$, the pFSHβ refers to a β subunit of the porcine FSH with a signal peptide removed; the colon represents the relationship that the porcine FSH β subunit and the porcine FSH α subunit are linked by a Van der Waals force; pFSHα refers to an α subunit of the porcine FSH with a signal peptide removed; L represents the linking relationship between the pFSHβ subunit and the Fc fragment; Fc refers to an Fc fragment of an immunoglobulin; and the subscript 2 outside of the parenthesis represents that pFSH-Fc-2 is a divalent homodimer, and the amino acid sequence of the pFSHβ-L-Fc is shown in SEQ ID NO: 8, and the amino acid sequence of the pFSHα is shown in SEQ ID NO: 1, the method comprising:

artificially synthesizing genes encoding pFSHα, pFSHβ, pFSHα-L-Fc and pFSHβ-L-Fc, performing codon optimization, and cloning the codon optimized genes into eukaryotic expression vectors, respectively;

simultaneously transforming the pFSHα recombinant vector and pFSHβ-L-Fc recombinant vector into eukaryotic cells, and expressing in eukaryotic cells, and isolating and purifying the target protein; or simultaneously transforming the pFSHβ recombinant vector and pFSHα-L-Fc recombinant vector into eukaryotic cells, and expressing in eukaryotic cells, and isolating and purifying the target protein.

15. The method of claim 14, wherein the eukaryotic expression vector is pcDNA3.1, and the eukaryotic cells include 293 and CHO cells.

16. A fusion protein produced according to the method of claim 15.

17. A fusion protein produced according to the method of claim 14.

* * * * *